(12) United States Patent
Leitner et al.

(10) Patent No.: US 8,846,971 B2
(45) Date of Patent: Sep. 30, 2014

(54) METAL CARBAMATES FORMED FROM DIAMINOPHENYLMETHANE

(71) Applicant: BASF SE, Ludwigshafen (DE)

(72) Inventors: Andreas Leitner, Pittsburg, PA (US); Robert Baumann, Mannheim (DE); Wolfgang Siegel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/920,166

(22) Filed: Jun. 18, 2013

(65) Prior Publication Data

US 2013/0281727 A1    Oct. 24, 2013

Related U.S. Application Data

(62) Division of application No. 12/918,931, filed as application No. PCT/EP2009/053168 on Mar. 18, 2009, now Pat. No. 8,519,174.

(30) Foreign Application Priority Data

Mar. 18, 2008  (EP) .................................... 08152934

(51) Int. Cl.
*C07C 261/00*  (2006.01)
*C07C 269/00*  (2006.01)
*C07C 271/00*  (2006.01)
*C07C 271/28*  (2006.01)
*C07C 269/06*  (2006.01)

(52) U.S. Cl.
CPC ............. *C07C 269/06* (2013.01); *C07C 271/28* (2013.01)
USPC ........................................................ 560/25

(58) Field of Classification Search
CPC .. C07C 271/28; C07C 271/66; C07C 269/02; C07C 271/20
See application file for complete search history.

(56) References Cited

U.S. PATENT DOCUMENTS

| | | |
|---|---|---|
| 3,763,217 A | 10/1973 | Brill |
| 4,268,683 A | 5/1981 | Gurgiolo |
| 4,268,684 A | 5/1981 | Gurgiolo |
| 4,395,565 A | 7/1983 | Romano |
| 4,550,188 A | 10/1985 | Frulla et al. |

FOREIGN PATENT DOCUMENTS

| | | |
|---|---|---|
| CA | 1166649 | 1/1984 |
| DE | 32 02 690 | 8/1982 |
| DE | 3627257 | 2/1988 |
| EP | 0 048 371 | 3/1982 |
| EP | 0 391 473 | 10/1990 |
| WO | 98 55451 | 12/1998 |
| WO | 98 56758 | 12/1998 |
| WO | 2007 015852 | 2/2007 |

OTHER PUBLICATIONS

International Search Report issued May 20, 2009 in PCT/EP09/053168 filed Mar. 18, 2009.

*Primary Examiner* — Rosalynd Keys
*Assistant Examiner* — Jennifer C Sawyer
(74) *Attorney, Agent, or Firm* — Oblon, Spivak, McClelland, Maier & Neustadt, L.L.P.

(57) ABSTRACT

The invention provides metal carbamates of the general formula (I)

(I)

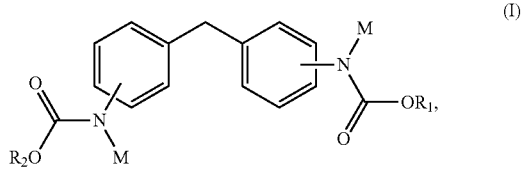

where $R_1$ and $R_2$ are each an alkyl group.

18 Claims, No Drawings

METAL CARBAMATES FORMED FROM DIAMINOPHENYLMETHANE

REFERENCE TO PRIOR APPLICATIONS

This application is a Divisional of U.S. application Ser. No. 12/918,931, filed Aug. 23, 2010; which is a 371 of PCT/EP09/53168, filed Mar. 18, 2009, and priority to European patent application 08152934.9, filed Mar. 18, 2008, is claimed, of which the entire content is incorporated herein by reference.

DESCRIPTION

The invention provides metal carbamates formed from diaminophenylmethane (MDA) and a process for preparing them.

Carbamates and the preparation and use thereof are known.

For the preparation of carbamates and urethanes, a series of processes is known.

In these processes, for example, Lewis acids, for example uranium salts (U.S. Pat. No. 3,763,217), aluminum turnings with iodine and Hg promoters (U.S. Pat. No. 4,550,188), zinc salts, iron salts, antimony salts and tin salts (U.S. Pat. Nos. 4,268,683, 4,268,684, EP 391473), are used as catalysts. A disadvantage for the industrial use of these processes are the sometimes low conversions, low selectivities or both.

High selectivities and yields are obtained, for example, in processes catalyzed with Lewis acids (Pb salts as catalysts), when a high excess of dialkyl carbonate (amine:carbonate 1:20) is used (WO 98/55451, WO 98/56758). The high excess of dialkyl carbonate leads to large recycle streams.

In other cases, high yields of urethane can be achieved when the urea formed in the urethanization is redissociated thermally to the corresponding urethane in an additional reaction (EP 048371 (catalysts: lead salts, titanium salts, zinc salts and zirconium salts), EP 391473 (catalyst: Zn salts)). The redissociation requires an additional, energy-intensive step.

A further disadvantage in the case of use of Lewis acids as homogeneous catalysts is the catalyst residues which remain in the product and can be removed only incompletely.

WO 2007/015852 describes the use of Lewis acidic heterogeneous catalysts for the urethanization of aromatic amines. This dispenses with a complicated removal of a homogeneous catalyst. The resulting conversions are too low for industrial scale applications and decrease together with the selectivity with increasing lifetime of the heterogeneous catalyst.

It is also known that urethanes can be prepared from aromatic amines using basic compounds, for example, alkali metal or alkaline earth metal alkoxides.

DE 3202690 describes the preparation of aromatic urethanes by reaction of aniline and dialkyl carbonates in the presence of a small amount of a metal alkoxide as a catalyst. The conversions described in the examples are incomplete and the selectivities achieved are insufficient for an industrial application.

Journal of Organic Chemistry, 2005, 70, 2219-2224 describes the reaction of aniline with a large excess of dimethyl carbonate (40-fold excess) in the presence of an excess of base such as sodium methoxide (NaOMe) or potassium tert-butoxide (KOtBu). With NaOMe, a selectivity of 67% after a reaction time of 210 min was obtained. With KOtBu, a selectivity after 1 min of 100% is described, which, however, declines to 60% through formation of the N-methylcarbanilate by-product with increasing reaction time. Conversions and isolated yields were not described.

N-arylcarbamates can be converted to isocyanates. Such processes are common knowledge. This procedure allows diisocyanates to be prepared by a phosgene-free route. Such processes are used to prepare aliphatic diisocyanates in particular.

In the case of aromatic diisocyanates, preparation by a phosgene-free process is difficult, since a series of side reactions proceed owing to the high reactivity of the aromatic compounds. However, it would be desirable if aromatic diisocyanates, which are industrially of great significance, were also preparable by phosgene-free processes.

It was an object of the present invention to find a simple means of providing starting materials for the preparation of aromatic diisocyanates by a phosgene-free process, which can be prepared with a high selectivity, a high yield and with high purity.

It has been found that, surprisingly, it is possible to isolate metal carbamates based on diaminophenylmethane (MDA) in pure form. After reaction with protic compounds, especially with alcohols or preferably with water, these can be converted to the corresponding diurethane (MDU) and, in a subsequent step, by thermal cleavage to MDI (methylene diphenyl diisocyanate).

The invention accordingly provides metal carbamates of the general formula (I)

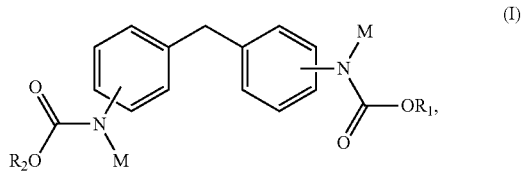

(I)

where $R_1$ and $R_2$ are the same or different and are each an alkyl group having 1-18 carbon atoms and M is an alkali metal atom.

Particular preference is given to alkyl groups having 2-7 carbon atoms, which may be branched, unbranched or cyclic, especially branched or unbranched.

In a preferred embodiment of the invention the $R_1$ and $R_2$ groups are identical.

The invention further provides a process for preparing metal carbamates of the general formula (I) by reacting
  a) diamino diphenylmethane with
  b) an alkyl carbonate of the general formula (II)

(II)

where $R_1$ and $R_2$ are each as defined above and
  c) a metal compound of the general formula (III)
    $M(R_3)n$
  where
    M is an alkali metal atom,
    $R_3$ are the same as $OR_1$ and $OR_2$, or are an amide or an alkylsilazide and
    n is equal to 1.

In one embodiment of the invention the alkyl chain $R_1$ and/or $R_2$ is modified with heteroatoms. The heteroatoms may be halogen atoms, preferably fluorine atoms and/or chlorine atoms, more preferably fluorine atoms. In another embodiment, the heteroatoms are oxygen atoms. These are preferably present in the form of ether groups.

It has been found that the urethanes which have been prepared using diaklyl carbonates having heteroatoms in the alkyl group can be cleaved particularly readily to form isocyanates.

$R_1$ and/or $R_2$ is preferably an ethyl, propyl, butyl, 2-methylpropyl, 3-methylbutyl, n-pentyl, 2-methoxyethyl, 2-ethoxyethyl or a 2,2,2-trifluoroethyl group.

$R_1$ and $R_2$ are more preferably identical. This has the advantage that, in the course of preparation of the inventive products (I) and in the course of any further processing to urethanes and conversion thereof to isocyanates, fewer products are in the process.

The compounds of the general formula (I) are solid at room temperature and can be removed from the reaction solution without any problem and in high purity. If required, they can be purified in a further process step.

The compounds of the general formula (I) are prepared, as described above, by reaction of components a), b) and c).

The diaminophenylmethane (MDA) used may be any isomers in any mixing ratios. Preference is given to using 2,4'-diaminophenylmethane, 4,4'-diaminophenylmethane, 2,2'-diaminophenylmethane and higher homologs (polyaminopolyphenylmethanes) and isomer mixtures.

In a preferred embodiment of the invention, the dialkyl carbonates b) are selected from the group comprising diethyl carbonate, di-n-propyl carbonate, di-n-butyl carbonate, di-2-methylpropyl carbonate, di-3-methylbutyl carbonate, di-n-pentyl carbonate, bis-2-methoxyethyl carbonate, bis-2-ethoxyethyl carbonate, bis-2,2,2-trifluoroethyl carbonate.

The metal compound c) preferably comprises basic organic metal compounds, especially compounds of alkali metals. They may, for example, be compounds comprising nitrogen atoms, for example amides, such as sodium amide or compounds comprising silicon atoms and nitrogen atoms, for example lithium hexamethyldisilazide.

The base more preferably comprises the alkoxides of alkali metals. The alkali metal M is preferably lithium, sodium or potassium. The alcohol radicals preferably corresponds to those of the alkyl carbonates of the general formula (II) used.

The compounds of the general formula (I) are prepared preferably under standard pressure at temperatures between 100 and 150° C. The yield of the process is between 95-100%.

In the reaction, the ratio of carbonate groups to amino groups is from 1:1 to 10:1, more preferably from 2:1 to 3:1.

The metal compound c) is preferably used in a stoichiometric amount, more preferably in a molar ratio of 1:1, based on the amino groups, i.e. in a ratio of about one mole of base per amino group.

The inventive metal carbamates may, as described, be converted to pure MDU by reprotonation with water.

The fact that a simple process would be able to prepare pure metal carbamates and the object of the invention would thus be achieved was not foreseeable to the person skilled in the art.

It was also unnecessary to work with a high excess of component b). In spite of the different reactivity of the two amino groups of the MDA, there was homogeneous conversion of the two amino groups.

The invention claimed is:

1. A process for preparing methylenediphenyldiurethane, the process comprising:
reacting a compound of water with a metal carbamate of formula (I):

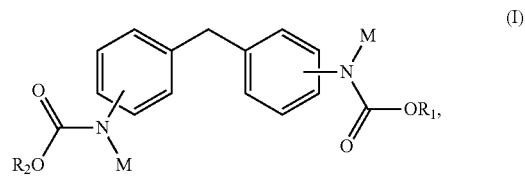

wherein:
$R_1$ and $R_2$ are each independently an alkyl group comprising 1 to 18 carbon atoms; and
M is an alkali metal ion.

2. The process of claim 1, wherein, in formula (I), the alkyl groups $R_1$ and $R_2$ each comprise 2-18 carbon atoms in the chain.

3. The process of claim 1, wherein, in formula (I), the alkyl groups $R_1$ and $R_2$ each comprise 2-7 carbon atoms in the chain.

4. The process of claim 1, wherein, in formula (I), the alkyl groups $R_1$ and $R_2$ are each independently an ethyl, propyl, butyl, 2-methylpropyl, 3-methylbutyl, n-pentyl, 2-methoxyethyl, 2-ethoxyethyl, or a 2,2,2-trifluoroethyl group.

5. The process of claim 1, wherein, in formula (I), the alkyl groups $R_1$ and $R_2$ comprise heteroatoms.

6. The process of claim 5, wherein the heteroatoms are halogen atoms.

7. The process of claim 5, wherein the heteroatoms are fluorine atoms.

8. The process of claim 5, wherein the heteroatoms are chlorine atoms.

9. The process of claim 5, wherein the heteroatoms are oxygen atoms.

10. The process of claim 5, wherein the heteroatoms are oxygen atoms present in the form of ether groups.

11. The process of claim 1, wherein, in formula (I), the alkali metal ion is lithium.

12. The process of claim 1, wherein, in formula (I), the alkali metal ion is sodium.

13. The process of claim 1, wherein, in formula (I), the alkali metal ion is potassium.

14. The process of claim 1, wherein, in formula (I), wherein $R_1$ and $R_2$ are identical.

15. The process of claim 2, wherein, in formula (I), $R_1$ and $R_2$ are identical.

16. The process of claim 3, wherein, in formula (I), $R_1$ and $R_2$ are identical.

17. The process of claim 4, wherein, in formula (I), $R_1$ and $R_2$ are identical.

18. The process of claim 5, wherein, in formula (I), $R_1$ and $R_2$ are identical.

* * * * *